US011229407B2

(12) United States Patent
Hitt et al.

(10) Patent No.: US 11,229,407 B2
(45) Date of Patent: Jan. 25, 2022

(54) SYSTEMS AND METHODS TO DETERMINE A RISK FACTOR RELATED TO DEHYDRATION AND THERMAL STRESS OF A SUBJECT

(71) Applicant: GoX Studio, Inc., Phoenix, AZ (US)

(72) Inventors: Joseph Karl Hitt, Scottsdale, AZ (US); Robert Bruce Floersheim, West Chester, PA (US)

(73) Assignee: GoX Studio, Inc., Phoenix, AZ (US)

( * ) Notice: Subject to any disclaimer, the term of this patent is extended or adjusted under 35 U.S.C. 154(b) by 0 days.

(21) Appl. No.: 16/895,916

(22) Filed: Jun. 8, 2020

(65) Prior Publication Data

US 2021/0378600 A1  Dec. 9, 2021

(51) Int. Cl.
*A61B 5/00* (2006.01)
*A61B 5/0205* (2006.01)
*A61B 5/11* (2006.01)

(52) U.S. Cl.
CPC ........ *A61B 5/7275* (2013.01); *A61B 5/02055* (2013.01); *A61B 5/4866* (2013.01);
(Continued)

(58) Field of Classification Search
CPC ... A61B 5/7275; A61B 5/7246; A61B 5/4866; A61B 5/02055; A61B 5/4875; A61B 5/7278; A61B 2560/0475; A61N 5/1112
See application file for complete search history.

(56) References Cited

U.S. PATENT DOCUMENTS 7,027,621 B1  4/2006 Prokoski
9,579,060 B1  2/2017 Lisy
(Continued)

FOREIGN PATENT DOCUMENTS

WO  WO-2017165037 A1 *  9/2017  ........... A61B 5/1118

OTHER PUBLICATIONS

Definition of correlate. Merriam-Webster Dictionary, retrieved on May 18, 2021; Retrieved from the Internet: <https://www.merriam-webster.com/dictionary/correlate> (Year: 2021).*
(Continued)

*Primary Examiner* — Gary Jackson
*Assistant Examiner* — Sebastian X Lukjan
(74) *Attorney, Agent, or Firm* — Esplin & Associates, PC

(57) ABSTRACT

Systems and methods to determine a risk factor related to dehydration and thermal stress of a subject are disclosed. Exemplary implementations may: generate output signals, by one or more sensors worn on a body of a subject, conveying information related to one or more of location of the subject, motion of the subject, temperature of the subject, cardiovascular parameters of the subject; store information related to the subject; obtain the output signals; determine in an ongoing manner, from the output signals, values of a water loss metric that correlates with estimated percentage of bodyweight of the subject lost in water; obtain heat index information for a contextual environment surrounding the subject; determine in an ongoing manner, from the output signals, values of an exertion metric that correlates with exertion of the subject due to work; and determine in an ongoing manner values for an aggregated risk factor of the subject.

20 Claims, 3 Drawing Sheets

(52) U.S. Cl.
CPC .......... *A61B 5/4875* (2013.01); *A61B 5/7246* (2013.01); *A61B 5/7278* (2013.01); *A61B 5/1112* (2013.01); *A61B 2560/0475* (2013.01)

(56) References Cited

U.S. PATENT DOCUMENTS

| | | | |
|---|---|---|---|
| 9,980,112 B1 | 5/2018 | Newby | |
| 10,307,101 B1* | 6/2019 | Miller | A61B 5/14546 |
| 10,959,056 B1 | 3/2021 | Alsahlawi | |
| 11,055,979 B1 | 7/2021 | Hitt | |
| 2007/0158128 A1 | 7/2007 | Gratz | |
| 2007/0167162 A1 | 7/2007 | Kim | |
| 2009/0005652 A1 | 1/2009 | Kurtz | |
| 2011/0029465 A1 | 2/2011 | Ito | |
| 2011/0047508 A1 | 2/2011 | Metzler | |
| 2012/0001876 A1 | 1/2012 | Chervenka | |
| 2012/0143019 A1* | 6/2012 | Russell | G16H 50/20 600/301 |
| 2012/0249797 A1 | 10/2012 | Haddick | |
| 2014/0222522 A1 | 8/2014 | Chait | |
| 2015/0242769 A1 | 8/2015 | Kezeu | |
| 2015/0358043 A1 | 12/2015 | Jeong | |
| 2016/0038083 A1* | 2/2016 | Ding | A61B 5/1121 600/388 |
| 2016/0058364 A1* | 3/2016 | Ionescu | A61B 5/07 600/301 |
| 2016/0235374 A1 | 8/2016 | Miller | |
| 2016/0278700 A1* | 9/2016 | Lee | A61B 5/0205 |
| 2016/0292988 A1 | 10/2016 | McCleary | |
| 2017/0046496 A1 | 2/2017 | Johnstone | |
| 2017/0303187 A1 | 10/2017 | Crouthamel | |
| 2017/0319130 A1* | 11/2017 | Thomas | A61B 5/0022 |
| 2018/0033279 A1 | 2/2018 | Chong | |
| 2018/0081912 A1 | 3/2018 | Suleiman | |
| 2018/0144427 A1 | 5/2018 | Ebesu | |
| 2018/0147913 A1 | 5/2018 | Bergin | |
| 2018/0153463 A1* | 6/2018 | Nissila | A61B 5/4266 |
| 2018/0330302 A1 | 11/2018 | Peterson | |
| 2019/0008687 A1 | 1/2019 | Ishiura | |
| 2019/0073618 A1 | 3/2019 | Kanukurthy | |
| 2019/0117170 A1* | 4/2019 | Begtrup | A61B 5/4875 |
| 2019/0134396 A1* | 5/2019 | Toth | A61N 1/36 |
| 2019/0298261 A1 | 10/2019 | Savchenko | |
| 2019/0311809 A1 | 10/2019 | Young | |
| 2019/0343429 A1 | 11/2019 | Elhawary | |
| 2020/0194124 A1 | 6/2020 | Kramer | |
| 2020/0205747 A1* | 7/2020 | Mulligan | A61B 5/0531 |
| 2020/0260973 A1 | 8/2020 | Prstojevich | |
| 2020/0279339 A1 | 9/2020 | Akutagawa | |
| 2020/0302452 A1 | 9/2020 | Platt | |

OTHER PUBLICATIONS

Definition of value. Merriam-Webster Dictionary, retrieved on May 18, 2021; Retrieved from the Internet: <https://www.merriam-webster.com/dictionary/value> (Year: 2021).*

* cited by examiner

— SYSTEMS AND METHODS TO DETERMINE A RISK FACTOR RELATED TO DEHYDRATION AND THERMAL STRESS OF A SUBJECT

ACKNOWLEDGEMENT OF GOVERNMENT SUPPORT

This invention was made with United States (U.S.) government support under Contract No. W91CRB-11-D-0004 awarded by the U.S. Army Research Laboratory. The U.S. government has certain rights in the invention.

FIELD OF THE DISCLOSURE

The present disclosure relates to systems and methods to determine a risk factor related to dehydration and thermal stress of a subject.

BACKGROUND

By the time a worker is aware of their dehydration and/or feels hot, the worker's body has likely lost 2% of their body weight in water. At this time, replenishment of the lost water cannot occur quick enough to effectively cool the body. Dehydration and thermal stress of a body of a subject may affect cognitive function and consequently contribute to injury, poor decisions, lack of perception, and/or other negative effects.

SUMMARY

One aspect of the present disclosure relates to a system configured to predict dehydration and thermal stress of a subject. The subject may wear a plurality of sensors on their body by which data is collected about the subject. The data may include information related to the heart of the subject, oxygen consumption of the subject, motion of the subject, location of the subject, and/or other data. Based on the location of the subject, information related to ambient conditions of an environment the subject is in may be obtained. Based on the data collected, a percentage of bodyweight that the subject lost in water (i.e., sweat) may be determined. Further based on the data, work done by the subject may be determined. Based on the percentage of bodyweight lost in water, the work done, and the ambient conditions, an overall risk value may be determined that is indicative of how susceptible the subject is to thermal stress and dehydration at that moment. Such risk value may allow the subject to prevent future thermal stress and dehydration and thus avoid increasing their core body temperature, overexertion, and/or other negative effects.

One aspect of the present disclosure relates to a system configured to determine a risk factor related to dehydration and thermal stress of a subject. The system may include one or more hardware processors configured by machine-readable instructions, a sensor group of one or more sensors worn on a body of a subject, and an electronic storage. The electronic storage may be configured to store information related to the subject, the information conveyed by the output signals, and/or other information.

The machine-readable instructions may be configured by instruction components. The instruction components may include computer program components. The instruction components may include one or more of signal obtaining component, water loss component, ambient condition component, exertion component, oxygen determination component, work determination component, risk determination component, and/or other instruction components.

The sensor group of the one or more sensors may be configured to generate output signals. The output signals may convey information related to one or more of location of the subject, motion of the subject, temperature of the subject, cardiovascular parameters of the subject, and/or other information.

The signal obtaining component may be configured to obtain the output signals. The output signals may be analog signals, digital signals, and/or encodings.

The water loss component may be configured to determine in an ongoing manner, from the output signals, values of a water loss metric that correlates with estimated percentage of bodyweight of the subject lost in water.

The ambient condition component may be configured to obtain heat index information for a contextual environment surrounding the subject.

The exertion component may be configured to determine in an ongoing manner, from the output signals, values of an exertion metric that correlates with exertion of the subject due to work.

The risk determination component may be configured to determine in an ongoing manner values for an aggregated risk factor of the subject. The values of the aggregated risk factor may be determined by aggregating values of the water loss metric, the heat index information, and the exertion metric for the subject.

As used herein, the term "obtain" (and derivatives thereof) may include active and/or passive retrieval, determination, derivation, transfer, upload, download, submission, and/or exchange of information, and/or any combination thereof. As used herein, the term "effectuate" (and derivatives thereof) may include active and/or passive causation of any effect, both local and remote. As used herein, the term "determine" (and derivatives thereof) may include measure, calculate, compute, estimate, approximate, generate, and/or otherwise derive, and/or any combination thereof.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
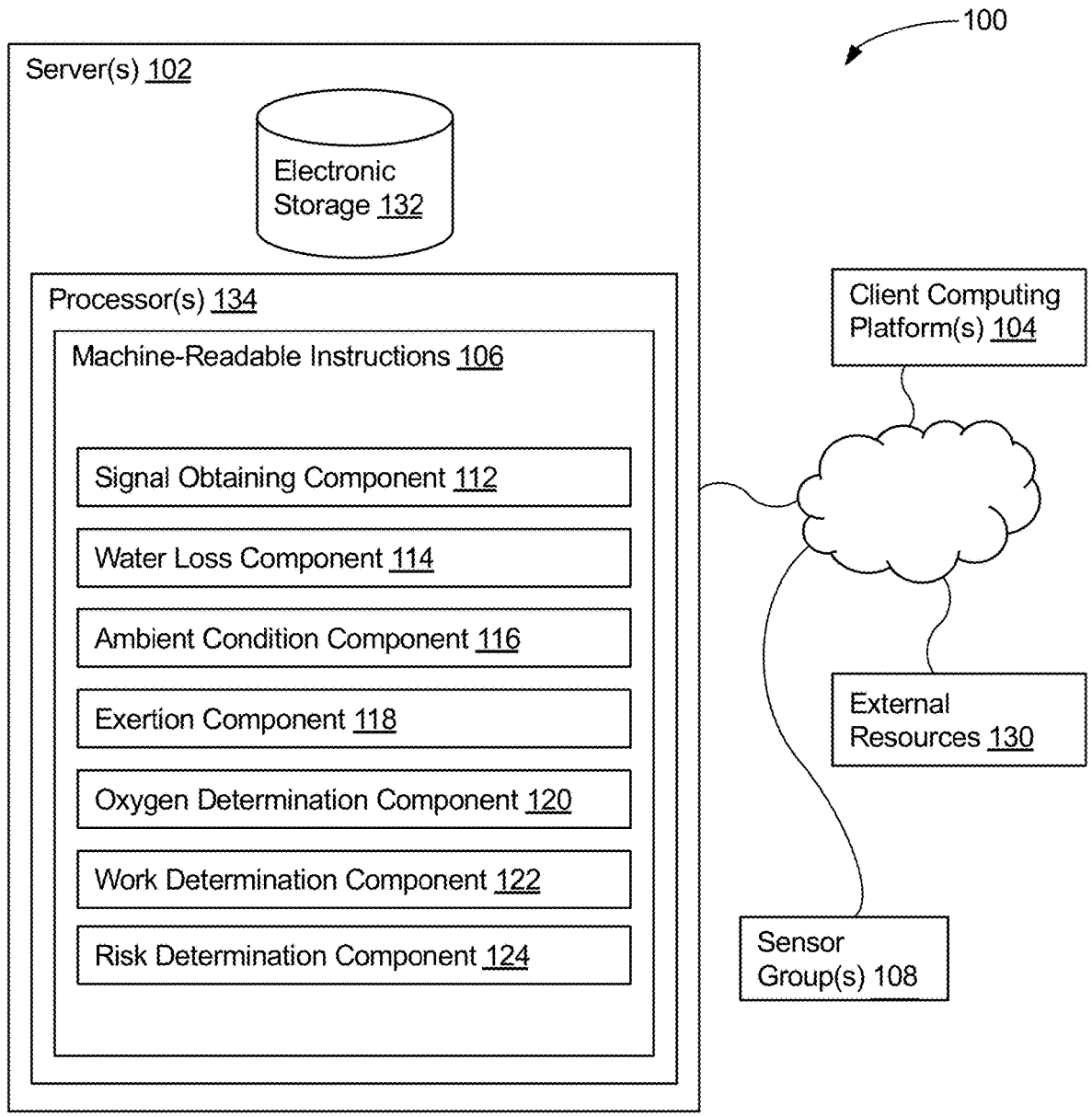
FIG. 1 illustrates a system configured to determine a risk factor related to dehydration and thermal stress of a subject, in accordance with one or more implementations.

FIG. 1 illustrates a system 100 configured to determine a risk factor related to dehydration and thermal stress of a subject, in accordance with one or more implementations. In some implementations, system 100 may include one or more servers 102. Server(s) 102 may be configured to communicate with one or more client computing platforms 104 and one or more sensor groups 108 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Server(s) 102 may be configured by machine-readable instructions 106. Machine-readable instructions 106 may include one or more instruction components. The instruction components may include computer program components. The instruction components may include one or more of signal obtaining component 112, water loss component 114, ambient condition component 116, exertion component 118, oxygen determination component 120, work determination component 122, risk determination component 124, and/or other instruction components.

Sensor group 108 may include one or more sensors worn on a body of a subject. The one or more sensors may be configured to generate output signals conveying information related to one or more of location of the subject, motion of the subject, temperature of the subject, cardiovascular parameters of the subject, and/or other information. The one or more sensors may include one or more of an orientation sensor, a location sensor, a pressure sensor, a temperature sensor, a light sensor, an audio sensor, cardiovascular sensor, and/or other sensors.

In some implementations, a location sensor may be configured to generate output signals conveying information related to the location of the subject and/or other information. The information related to the location derived from output signals of a location sensor may define one or more of a geo-location of the subject, an elevation of the subject, and/or other measurements. A location sensor may include one or more of a GPS, an altimeter, and/or other devices. The location of the subject may be a location of a contextual environment of the subject. The contextual environment may be the immediate space surrounding the subject and of which the subject is operating and/or working in. The immediate area may be a particular radius surrounding the subject defined by the location sensor, an operator user, the subject, and/or by other definition. The contextual environment may change over time upon obtainment of an assigned route and/or a predicted route of the subject.

The information related to the motion of the subject may include acceleration, orientation, speed of motion, joint angles, and/or other information related to the motion of the subject. An orientation sensor may be configured to generate output signals conveying orientation information and/or other information. Orientation information derived from output signals of an orientation sensor may define an orientation of the subject. In some implementations, orientation may refer to one or more of a pitch angle, a roll angle, a yaw angle, heading, pointing direction, and/or other measurements. An orientation sensor may include an inertial measurement unit (IMU) such as one or more of an accelerometer, a gyroscope, a magnetometer, Inclinometers, Electronic nose, Infrared Imagers, Micro-bolometers, micro-displays (DMD), Digital micro-mirror device, Optical Switches, and/or other devices.

A pressure sensor may be configured to generate output signals conveying pressure information and/or other information. Pressure information derived from output signals of a pressure sensor may define a force per unit area imparted to the pressure sensor. A pressure sensor may include one or more of a piezoresistive strain gauge, a capacitive pressure sensor, an electromagnetic pressure sensor, a piezoelectric sensor, a strain-gauge, and/or other pressure sensors.

A temperature sensor may be configured to generate output signals conveying information related to the temperature of the subject and/or other information. The information related to the temperature of the subject derived from output signals of a temperature sensor may define one or more of a temperature at the temperature sensor, temperature within a threshold range of the temperature sensor, biometric information, and/or other measure of temperature of the subject. The biometric information may include one or more of skin temperature readings, internal body temperature readings, and/or other readings. In some implementations, the information related to the temperature of the subject may define one or more of a temperature at the temperature sensor, temperature within a threshold range of the temperature sensor, and/or other measure of temperature of a contextual environment of the subject. A temperature sensor may include one or more of a thermocouple, a resistive temperature Measuring device, an infrared sensor, a bimetallic device, a thermometer, and/or other temperature sensors.

A light sensor may be configured to generate output signals conveying ambient light information and/or other information. The ambient light information derived from output signals of a light sensor may define intensity and/or presence (or absence) of light or other electromagnetic radiation incident on the light sensor. A light sensor may include one or more of a photodiode, an active-pixel sensor, photovoltaic, and/or other sensors.

An audio input sensor may be configured to receive audio input. An audio input sensor may include a sound transducer and/or other sensor configured to convert sound (e.g., air pressure variation) into an electrical signal. By way of non-limiting illustration, an audio input sensor may include a microphone.

One or more cardiovascular sensors may be configured to generate output signals conveying biometric information related to heart, lungs, and circulation of the subject. The biometric information may include values for the cardiovascular parameters of the subject, and/or other values for other biometric parameters. The cardiovascular parameters may include heart rate, a resting heart rate of the subject, a respiratory rate of the subject, blood pressure of the subject, oxygen saturation of the subject, heart variability, heartbeat strength, heartbeat rhythm, and/or other cardiovascular parameters. The one or more cardiovascular sensors may include one or more an electrodermal activity (EDA), an electrocardiography (EKG or ECG) sensor, a blood volume pulse (BVP) sensor, a respiration sensor, a blood pressure sensor, and/or other cardiovascular sensors. Other sensors that may convey the biometric information may include one or more of an electrodermal activity (EDA), an electromyography (EMG) sensor, and/or other sensors.

Electronic storage 132 may be configured to store information related to the subject, the information related to one or more of the location of the subject, the motion of the subject, the temperature of the subject, the cardiovascular parameters of the subject, other information conveyed by the output signals, and/or other information. The information related to the subject may include values that define subject parameters. The subject parameters may include gender, weight, height, age, race, underlying conditions, and/or other subject parameters.

Signal obtaining component 112 may be configured to obtain the output signals. The output signals may be analog signals, digital signals, encoded signals, combinations thereof, and/or other signals.

Ambient condition component 116 may be configured to obtain condition information related to the ambient conditions of the contextual environment surrounding the subject. The condition information may include values for condition parameters. The condition parameters may include one or more of a temperature, humidity, precipitation, an ultraviolet index, visibility, pressure, dew point, wind direction, wind gust, cloud coverage, and/or other condition parameters. Determining the values of the water loss metric may be based on work done by the subject and the condition information. In some implementations, the condition information may be stored to electronic storage 132. In some implementations, the condition information may be stored to electronic storage 132 and associated with a particular date and/or time.

Oxygen determination component 120 may be configured to determine current oxygen consumption of the subject. Such determination may be in an ongoing manner. Such determination may be from the output signals. Determining the current oxygen consumption may be based on information related to the motion of the subject, the ambient conditions of the contextual environment, the information related to the subject, the values of the cardiovascular parameters, and/or other information. The output signals used to determine the current oxygen consumption may convey information related to a volume of oxygen currently consumed by the subject at the particular moment in time. The current oxygen consumption may be stored to electronic storage 132 upon determination. In some implementations, the current oxygen consumption may be stored and associated with a corresponding date and/or time.

Oxygen determination component 120 may be configured to determine maximal oxygen consumption. The maximal oxygen consumption may characterize a maximum volume of oxygen the subject has ever consumed. Determining the maximal oxygen consumption may be from the output signals. In some implementations, determining the maximal oxygen consumption may be based on the information related to the subject (e.g., age, height, weight), the information related to the motion of the subject (e.g., speed of the motion), the condition information (e.g., a temperature value, and a humidity value) and/or other information. Determining the maximal oxygen consumption may include determining that a particular current oxygen consumption is the maximal oxygen consumption by comparing the particular oxygen consumption with one or more of the current oxygen consumption stored in electronic storage 132 and defining the maximal oxygen consumption based on the comparison(s). The maximal oxygen consumption may be stored to electronic storage 132 upon determination. In some implementations, the maximal oxygen consumption may be stored and associated with a corresponding date and/or time.

Work determination component 122 may be configured to determine work exerted by the subject. The work exerted may be the product of force and displacement of an object. Determining the work exerted by the subject may be based on the information related to the motion of the subject, the values the cardiovascular parameters of the subject, the current oxygen consumption, weight of the object, displacement (e.g., height displacement) of the object, repetition of the motion of the subject, and/or other information. The weight of the object and the displacement of the object may be input prior to exertion of the work by the subject. For example, the subject may be instructed to move 100 35-pound cinderblocks. The weight of 35 pounds may be input and a repetition of 100 may be entered to determine the work exerted by the subject. Furthermore, the displacement of the object may be entered, such as 200 feet. The work exerted by the subject may be stored to electronic storage 132 upon determination. In some implementations, the work exerted by the subject may be stored and associated with a corresponding date and/or time.

Water loss component 114 may be configured to determine values of a water loss metric that correlate with estimated percentage of bodyweight of the subject lost in water. Determining the values of the water loss metric may be in an ongoing manner. The term "ongoing manner" as used herein may refer to continuing to perform an action (e.g., determine) periodically (e.g., every 30 seconds, every minute, every hour, etc.) until receipt of an indication to terminate. The indication to terminate may include powering off client computing platform 104, charging one or more of a battery of client computing platform 104, resetting client computing platform 104, and/or other indications of termination. As used herein, the term "correlate" (and derivatives thereof) may include estimate, quantify, correspond to, combinations thereof, and/or other terms that refer to a relationship in which one value indicates another value. Determining the values of the water loss metric may be from the output signals. The water loss metric may be a system of measurement of how much water (e.g., sweat) the subject has lost. Determining the values of the water loss metric may be based on the work done by the subject, the condition information, and/or other information. Determining the values of the water loss metric may include forecast modeling, time series modeling, average risk prediction modeling, weighted average modeling, machine learning, combinations thereof, and/or other determination techniques. The values of the water loss metric may indicate the estimated percentage, or otherwise estimated amount, of bodyweight loss of the subject. The values of the water loss metric may be stored to electronic storage 132. In some implementations, the values of the water loss metric may be stored to electronic storage 132 and associated with a particular date and/or time.

Ambient condition component 116 may be configured to obtain heat index information for a contextual environment surrounding the subject. The heat index information may include values for a current heat index, a future heat index, and/or other information. In some implementations, a heat index be a temperature of the contextual environment of the subject. In some implementations, the heat index may account for air temperature, relative humidity, the wind gust, and/or one or more of the condition parameter values to presume a temperature at which the contextual environment that surrounds the subject feels. As such, the current heat index may represent a current temperature of the contextual environment that surrounds the subject. The future heat index may represent a future temperature the contextual environment may reach on a particular day. The future heat index may represent a future peak temperature of which may be the highest temperature of the particular day. In some implementations, ambient condition component 116 may be configured to determine, or otherwise derive, one or more values for a heat index metric, based on the heat index information. The one or more values for the heat index metric may correlate with the current heat index and the future heat index. In some implementations, the heat index information obtained may include the one or more values for the heat index metric. The heat index information and the one or more values for the heat index metric may be stored to electronic storage 132. In some implementations, the heat index information and the one or more values for the heat index metric may be stored to electronic storage 132 and associated with a particular date and/or time.

Exertion component 118 may be configured to determine heart rate. Such determination may be in an ongoing manner. Such determination may be from the output signals. Determining the heart rate may be based on information related to the motion of the subject, the ambient conditions of the contextual environment, the information related to the subject, values of the cardiovascular parameters, and/or other information. The output signals used to determine the heart rate may convey information related to values of the cardiovascular parameters. The values of the cardiovascular parameters may define one or more of a resting heart rate, a respiratory rate, blood pressure, oxygen saturation in blood, and/or other measurements of the heart of the subject. The heart rate of the subject may indicate beats per minute, heart rate variability, heartbeat strength, heartbeat rhythm, and/or other information. The heart rate determined may be a current heart rate at a particular moment in time. The heart rate determined may be stored to electronic storage 132. In some implementations, the heart rate determined may be stored to electronic storage 132 and associated with a particular date and/or time.

Exertion Component 118 may be configured to determine values of an exertion metric. The values of the exertion metric may correlate with exertion of the subject due to the work. The exertion of the subject may be the use the energy by the subject due to the work exerted by the subject. Thus, the exertion metric may be system of measurement of how much work (e.g., lifting) the subject has done or exerted. Determining the values of the exertion metric may be in an ongoing manner. Determining the values of the exertion metric may from the output signals. Determining the values of the exertion metric may be based on the heart rate, the current oxygen consumption, the work done by the subject, and/or other information. The values of the exertion metric may be stored to electronic storage 132. In some implementations, the values of the exertion metric may be stored to electronic storage 132 and associated with a particular date and/or time.

Risk determination component 124 may be configured to determine values for an aggregated risk factor of the subject. Determining the aggregated risk factor may be in an ongoing manner. The values of the aggregated risk factor may be determined by aggregating values of the water loss metric, the heat index information, the exertion metric for the subject, and/or other information. The values of the aggregated risk factor may indicate a risk related to thermal stress and dehydration that the subject is susceptible to. Dehydration in addition to thermal stress of the body of the subject may include an increase in core body temperature, an increase in heart rate, an increase in oxygen consumption, a decrease in work, a decrease in efficiency of the work, a global cardiopulmonary and neural muscular chain reaction that may decrease cardiac output, stroke volume, cognitive function, and mechanical output, and/or other negative effects. The values of the aggregated risk factor may be part of a range of risk. For example, the range of risk may span from 0 to 100. The values for an aggregated risk factor may be a value be within the range such as 15. The range of risk may include one or more thresholds. The one or more threshold may indicate different levels of risk such as no risk, moderate risk, and dangerous risk. A threshold may be associated with a particular value of the aggregated risk factor. For example, for a moderate risk of thermal stress and dehydration, the value of the aggregated risk factor must be at least 20. For example, for a dangerous risk of thermal stress and dehydration, the value of the aggregated risk factor must be at least 40. Determining the aggregated risk factor of the subject may include forecast modeling, time series modeling, average risk prediction modeling, weighted average modeling, machine learning, combinations thereof, and/or other determination techniques. The values for the aggregated risk factor may be stored to electronic storage 132. In some implementations, the values for the aggregated risk factor may be stored to electronic storage 132 and associated with a particular date and/or time.

Risk determination component 124 may be configured to determine values for a fatigue risk. The values of the fatigue risk may be indicative of an increase in tiredness, lethargy, exhaustion, and/or other factors that the subject is susceptible to. Furthermore, in some implementations, the values of the fatigue risk may be indicative of a decrease in perception, performance, motivation, and/or other factors that the subject is susceptible to. The values of the fatigue risk may be part of a range of fatigue risk. For example, the range of fatigue risk may span from 0 to 100. The values for the fatigue risk may a value be within the range such as 35. The range of fatigue risk may include one or more thresholds. The one or more threshold may indicate different levels of risk such as no risk, moderate risk, and dangerous risk. A threshold may be associated with a particular value of the fatigue risk. Determining the values for the fatigue risk may be in an ongoing manner. Determining the values for the fatigue risk may include dividing the current oxygen consumption by the maximal oxygen consumption. A value of the fatigue risk may correlate to recovery time of the subject. The recovery time may be the length of time required for the body of the subject (e.g., muscles, tissues, etc.) to repair, rebuild, and/or strengthen. As such, the higher or more dangerous the values of the fatigue risk, the longer recovery time of the subject may be. The values for the fatigue risk may be stored to electronic storage 132. In some implementations, the values for the fatigue risk may be stored to electronic storage 132 and associated with a particular date and/or time.

Figure 3:
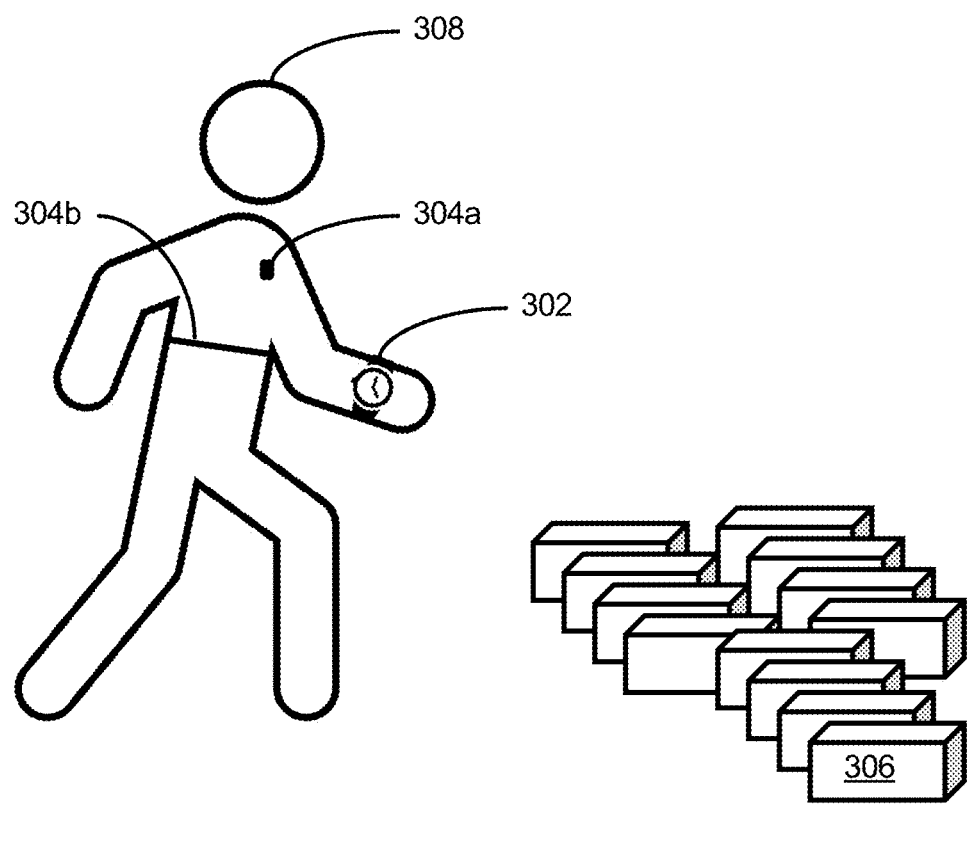
FIG. 3 illustrates an example implementation of a system configured to determine a risk factor related to dehydration and thermal stress of a subject, in accordance with one or more implementations.

FIG. 3 may illustrate an example implementation of a system configured to determine a risk factor related to dehydration and thermal stress of a subject, in accordance with one or more implementations. FIG. 3 may include subject 308 whom of which is moving bricks 306 in environment 300. By way of non-limiting example, subject 308 may be a solider, a maintenance worker, or otherwise a subject that may exert a copious amount of energy. Subject 308 may be wearing on their body a Smartwatch 302, sensor 304a, and sensor 304b. Sensor 304a may be located near the heart of subject 300. Sensor 304b may be located around the chest of subject 308. Contemporaneous to and due to subject 308 moving bricks 306, a value of a water loss metric that correlates with a percentage in bodyweight lost in water by subject 308 may be determined. Furthermore, the heat index information may be obtained for environment 300. The heat index information may include a value of the heat index metric that indicates a temperature of 90 degrees Fahrenheit in environment 300. Contemporaneous to and due to subject 308 moving bricks 306, a value for the exertion metric may be determined that correlates with exertion by subject 308 due to work. Based on the value of the water loss metric, the heat index information, and the value of the exertion metric, a value for the aggregated risk factor may be determined that indicates how susceptible subject 308 is the thermal stress and/or dehydration. The value for the aggregated risk factor may, for example, be presented on Smartwatch 302.

In some implementations, server(s) 102, client computing platform(s) 104, and/or external resources 130 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 130 may be operatively linked via some other communication media.

A given client computing platform 104 may include one or more processors configured to execute computer program components. The computer program components may be configured to enable an expert or user associated with the given client computing platform 104 to interface with system 100 and/or external resources 130, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, a Smartwatch, a gaming console, and/or other computing platforms.

For example, in some implementations, the subject may wear a first client computing platform that is a Smartwatch. A first sensor group may include one or more of the sensors worn on one or more parts of the body of the subject. One or more of the sensors included in the first sensor group may be worn on a wrist, a wrist via the first client computing platform, upper chest, lower chest, upper arm, around the neck, abdomen, and/or other parts of the body of the subject.

External resources 130 may include sources of information outside of system 100, external entities participating with system 100, and/or other resources. In some implementations, some or all of the functionality attributed herein to external resources 130 may be provided by resources included in system 100.

Server(s) 102 may include electronic storage 132, one or more processors 134, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 132 may comprise non-transitory storage media that electronically stores information. The electronic storage media of electronic storage 132 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 132 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 132 may include one or more virtual storage resources (e.g., cloud storage, a virtual private network, and/or other virtual storage resources). Electronic storage 132 may store software algorithms, information determined by processor(s) 134, information received from server(s) 102, information received from client computing platform(s) 104, and/or other information that enables server(s) 102 to function as described herein.

Processor(s) 134 may be configured to provide information processing capabilities in server(s) 102. As such, processor(s) 134 may include one or more of a digital processor, an analog processor, a digital circuit designed to process information, an analog circuit designed to process information, a state machine, and/or other mechanisms for electronically processing information. Although processor(s) 134 is shown in FIG. 1 as a single entity, this is for illustrative purposes only. In some implementations, processor(s) 134 may include a plurality of processing units. These processing units may be physically located within the same device, or processor(s) 134 may represent processing functionality of a plurality of devices operating in coordination. Processor(s) 134 may be configured to execute components 112, 114, 116, 118, 120, 122, and/or 124, and/or other components. Processor(s) 134 may be configured to execute components 112, 114, 116, 118, 120, 122, and/or 124, and/or other components by software; hardware; firmware; some combination of software, hardware, and/or firmware; and/or other mechanisms for configuring processing capabilities on processor(s) 134. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 112, 114, 116, 118, 120, 122, and/or 124 are illustrated in FIG. 1 as being implemented within a single processing unit, in implementations in which processor(s) 134 includes multiple processing units, one or more of components 112, 114, 116, 118, 120, 122, and/or 124 may be implemented remotely from the other components. The description of the functionality provided by the different components 112, 114, 116, 118, 120, 122, and/or 124 described below is for illustrative purposes, and is not intended to be limiting, as any of components 112, 114, 116, 118, 120, 122, and/or 124 may provide more or less functionality than is described. For example, one or more of components 112, 114, 116, 118, 120, 122, and/or 124 may be eliminated, and some or all of its functionality may be provided by other ones of components 112, 114, 116, 118, 120, 122, and/or 124. As another example, processor(s) 134 may be configured to execute one or more additional components that may perform some or all of the functionality attributed below to one of components 112, 114, 116, 118, 120, 122, and/or 124.

Figure 2:
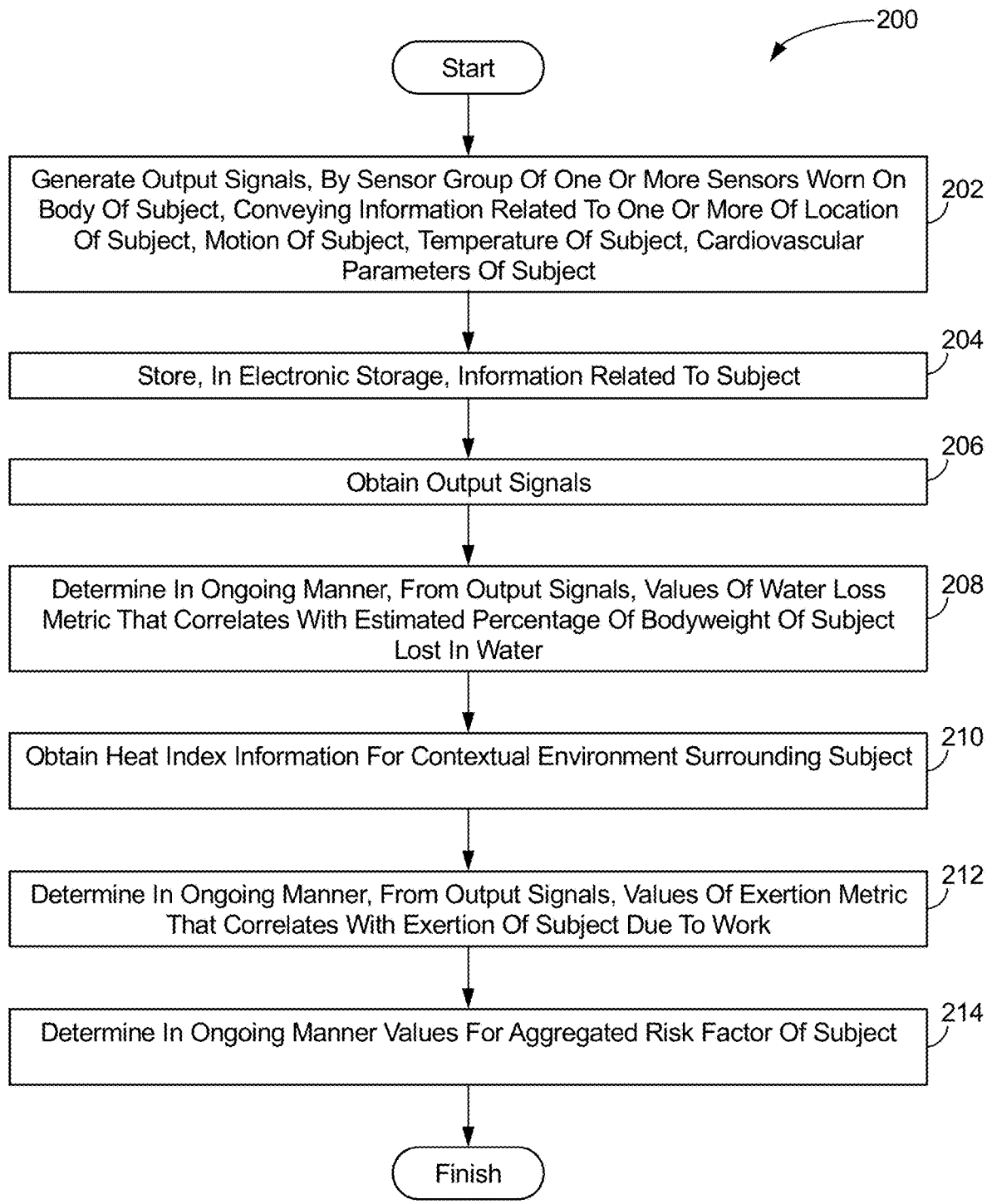
FIG. 2 illustrates a method to determine a risk factor related to dehydration and thermal stress of a subject, in accordance with one or more implementations.

FIG. 2 illustrates a method 200 to determine a risk factor related to dehydration and thermal stress of a subject, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include generating output signals, by a sensor group of one or more sensors worn on a body of a subject, conveying information related to one or more of location of the subject, motion of the subject, temperature of the subject, cardiovascular parameters of the subject. Operation 202 may be performed by one or more hardware processors configured by machine-readable instructions including a component that is the same as or similar to sensor group 108, in accordance with one or more implementations.

An operation 204 may include storing, in electronic storage, information related to the subject. Operation 204 may be performed by one or more hardware processors configured by machine-readable instructions including a component that is the same as or similar to water loss component 114, ambient condition component 116, exertion component 118, oxygen determination component 120, work determination component 122, and/or risk determination component 124, and electronic storage 132, in accordance with one or more implementations.

An operation 206 may include obtaining the output signals. Operation 206 may be performed by one or more hardware processors configured by machine-readable instructions including a component that is the same as or similar to signal obtaining component 112, in accordance with one or more implementations.

An operation 208 may include determining in an ongoing manner, from the output signals, values of a water loss metric that correlates with estimated percentage of bodyweight of the subject lost in water. Operation 208 may be performed by one or more hardware processors configured by machine-readable instructions including a component that is the same as or similar to water loss component 114, in accordance with one or more implementations.

An operation 210 may include obtaining heat index information for a contextual environment surrounding the subject. Operation 210 may be performed by one or more hardware processors configured by machine-readable instructions including a component that is the same as or similar to ambient condition component 116, in accordance with one or more implementations.

An operation 212 may include determining in an ongoing manner, from the output signals, values of an exertion metric that correlates with exertion of the subject due to work. Operation 212 may be performed by one or more hardware processors configured by machine-readable instructions including a component that is the same as or similar to exertion component 118, in accordance with one or more implementations.

An operation 214 may include determining in an ongoing manner values for an aggregated risk factor of the subject. The values of the aggregated risk factor may be determined by aggregating values of the water loss metric, the heat index information, and the exertion metric for the subject. Operation 214 may be performed by one or more hardware processors configured by machine-readable instructions including a component that is the same as or similar to risk determination component 124, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to determine a risk factor related to dehydration and thermal stress of a subject, the system comprising:
   a sensor group of sensors worn on a body of a subject, configured to generate output signals conveying information related to one or more of: location of the subject, motion of the subject, temperature of the subject, cardiovascular parameters of the subject;
   electronic storage configured to store the information related to the subject; and
   one or more processors configured by machine-readable instructions to:
      obtain the output signals;
      determine in an ongoing manner, from the output signals, values of a water loss metric that quantify an estimated percentage of bodyweight of the subject lost in water;
      obtain heat index information for a contextual environment surrounding the subject;
      determine in an ongoing manner, from the output signals, values of an exertion metric that quantifies exertion of the subject due to work, wherein the exertion metric is separate and discrete from the water loss metric; and
      determine, in an ongoing manner, individual values for an aggregated risk factor of the subject that indicates risk of thermal stress and dehydration of the subject at a given point in time, wherein the values of the aggregated risk factor are determined by aggregating values of the water loss metric, the heat index information, and the exertion metric for the subject.

2. The system of claim 1, wherein the one or more processors are further configured to:
   determine in an ongoing manner, from the output signals, heart rate and current oxygen consumption of the subject based on information related to the motion of the subject, ambient conditions of the contextual environment, and the information related to the subject; and wherein determining the values of the exertion metric is based on the heart rate and the current oxygen consumption.

3. The system of claim 2, wherein the output signals used to determine the heart rate convey information related to values of the cardiovascular parameters.

4. The system of claim 2, wherein the output signals used to determine the current oxygen consumption convey information related to a volume of oxygen currently consumed by the subject.

5. The system of claim 2, wherein the one or more processors are further configured to:
determine, from the output signals, maximal oxygen consumption; and
determine in an ongoing manner values for a fatigue risk by dividing the current oxygen consumption by the maximal oxygen consumption, the fatigue risk correlating to recovery time of the subject.

6. The system of claim 5, wherein the maximal oxygen consumption characterizes the maximum volume of oxygen the subject has consumed.

7. The system of claim 2, wherein the one or more processors are further configured to:
determine the work based on information related to the motion of the subject, information related to the cardiovascular parameters of the subject, and the current oxygen consumption.

8. The system of claim 7, wherein the one or more processors are further configured to:
obtain condition information related to ambient conditions of the contextual environment surrounding the subject, wherein determining the values of the water loss metric is based on the work and the condition information.

9. The system of claim 1, wherein the heat index information includes a current heat index and a future heat index, wherein the one or more processors are further configured to:
determine a value for a heat index metric that correlates with the current heat index and the future heat index.

10. The system of claim 1, wherein determining in an ongoing manner values for the aggregated risk factor of the subject includes forecast modeling, time series modeling, average risk prediction modeling, and/or weighted average modeling.

11. A method to determine a risk factor related to dehydration and thermal stress of a subject, the method comprising:
generating output signals, by a sensor group of sensors worn on a body of a subject, conveying information related to one or more of: location of the subject, motion of the subject, temperature of the subject, cardiovascular parameters of the subject;
storing, in electronic storage, the information related to the subject;
obtaining, using one or more processors, the output signals;
determining in an ongoing manner, using the one or more processors, from the output signals, values of a water loss metric that quantify an estimated percentage of bodyweight of the subject lost in water;
obtaining heat index information, using the one or more processors, for a contextual environment surrounding the subject;
determining in an ongoing manner, using the one or more processors, from the output signals, values of an exertion metric that quantifies exertion of the subject due to work, wherein the exertion metric is separate and discrete from the water loss metric; and
determining in an ongoing manner, using the one or more processors, individual values for an aggregated risk factor of the subject that indicates risk of thermal stress and dehydration of the subject at a given point in time, wherein the values of the aggregated risk factor are determined by aggregating values of the water loss metric, the heat index information, and the exertion metric for the subject.

12. The method of claim 11, further comprising:
determine in an ongoing manner using the one or more processors, from the output signals, heart rate and current oxygen consumption of the subject based on information related to the motion of the subject, ambient conditions of the contextual environment, and the information related to the subject; and wherein determining the values of the exertion metric is based on the heart rate and the current oxygen consumption.

13. The method of claim 12, wherein the output signals used to determine the heart rate convey information related to values of the cardiovascular parameters.

14. The method of claim 12, wherein the output signals used to determine the current oxygen consumption convey information related to a volume of oxygen currently consumed by the subject.

15. The method of claim 12, further comprising:
determining, from the output signals, using the one or more processors, maximal oxygen consumption; and
determining in an ongoing manner, using the one or more processors, values for a fatigue risk by dividing the current oxygen consumption by the maximal oxygen consumption, the fatigue risk correlating to recovery time of the subject.

16. The method of claim 15, wherein the maximal oxygen consumption characterizes the maximum volume of oxygen the subject has consumed.

17. The method of claim 12, further comprising:
determining, using the one or more processors, the work based on information related to the motion of the subject, information related to the cardiovascular parameters of the subject, and the current oxygen consumption.

18. The method of claim 17, further comprising:
obtaining, using the one or more processors, condition information related to ambient conditions of the contextual environment surrounding the subject, wherein determining the values of the water loss metric is based on the work and the condition information.

19. The method of claim 11, wherein the heat index information includes a current heat index and a future heat index, further comprising:
determining, using the one or more processors, a value for a heat index metric that correlates with the current heat index and the future heat index.

20. The method of claim 11, wherein determining in an ongoing manner values for the aggregated risk factor of the subject includes forecast modeling, time series modeling, average risk prediction modeling, and/or weighted average modeling.

* * * * *